US00PP10428P

United States Patent [19]

Kientzler

[11] Patent Number: Plant 10,428

[45] Date of Patent: Jun. 2, 1998

[54] NEW GUINEA IMPATIENS PLANT 'KIJOLA'

[75] Inventor: Ludwig Kientzler, Gensingen, Germany

[73] Assignee: Paul Ecke Ranch, Inc., Encinitas, Calif.

[21] Appl. No.: 795,126

[22] Filed: Feb. 7, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named 'Kijola', but marketed under the synonym 'Jolana', characterized by its large magenta-colored flowers; freely flowering habit; upright and mounded growth habit; and dark green, glossy, non-variegated foliage.

2 Drawing Sheets

The present invention relates to a new and distinct cultivar of New Guinea Impatiens plant, botanically known as *Impatiens hawkeri*, which is to be internationally registered as 'Kijola'. It is anticipated that the plant will be marketed under the synonym 'Jolana'. Hereinafter the disclosed plant will be referred to as 'Jolana'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as P223 as the male, or pollen parent, with the proprietary seedling selection identified as P866 as the female, or seed patent. The cultivar Jolana was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Jolana'. These characteristics in combination distinguish 'Jolana' as a new and distinct cultivar:

1. Large magenta-colored flowers.
2. Freely flowering.
3. Upright and mounded growth habit.
4. Dark green, glossy, non-variegated foliage.

The new New Guinea Impatiens is similar in flower color to the New Guinea Impatiens cultivar 'Anguilla' (U.S. Plant patent applied for). However in side-by-side comparisons in Encinitas, Calif, under commercial practice, plants of the new New Guinea Impatiens differed from plants of the cultivar Anguilla in the following characteristics:

1. Plants of the new New Guinea Impatiens more upright than plants of the cultivar 'Anguilla'.
2. Plants of the new New Guinea Impatiens are more vigorous than plants of the cultivar 'Anguilla'.
3. Stems of plants of the new New Guinea Impatiens have longer internodes than stems of plants of the cultivar 'Anguilla'.
4. Leaves of plants of the new New Guinea Impatiens are larger than leaves of plants of the cultivar 'Anguilla'.
5. Plants of the new New Guinea Impatiens are more freely flowering than plants of the cultivar 'Anguilla'.
6. Flowers of plants of the new New Guinea Impatiens are larger than flowers of plants of the cultivar 'Anguilla'.

7. Flower spurs of plants of the new New Guinea Impatiens are longer than flower spurs of plants of the cultivar 'Angilla'.

A detailed comparison of plants of the new New Guinea Impatiens and the cultivar Anguilla appears in Chart A at the end of the specification.

The accompanying colored photographs illustrate the overall appearance of the new cultivar, showing the colors as true as it is reasonably possible to obtain in colred reproductions of this type.

The first photograph comprises a top perspective view of a typical plant of 'Jolana'.

The second photograph comprises a close-up view of typical flowers and leaves of the varieties Anguilla (top of photo) and Jolana (bottom of photo).

The flower and foliage colors in the photographs may differ from the actual colors due to light reflectance.

The cultivar 'Jolana' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C and night tempertures ranging from 16 to 18C with light levels averaging 3,000 footcandles.

In the following descriptions, color references are made to The Royal Horticultural Society Colour Chart except where general terms of ordinary dictionary significance are used.

Classification:

*Botanical.*—*Impatiens hawkeri.*

*Commercial.*—New Guinea Impatiens 'Kijola', but marketed under 'Jolana'.

Parentage:

*Male parent.*—Proprietary seedling selection P223.

*Female parent.*—Proprietary seedling selection P866.

Propagation:

*Type cutting.*—Terminal cuttings.

*Time to initiate roots.*—About 15 days with 21C soil temperature.

Plant description:

*Plant form.*—Upright and mounded.

*Growth habit.*—Moderately vigorous to vigorous. Moderate branching. Suitable for 10 to 25-cm containers.

*Plant size.*—Height: About 20 cm. Width or spread: About 27 cm.

*Lateral Branches.*—Quantity: Five to seven. Size: Length: About 10 cm. Diameter: About 9 mm. Internode length: About 5.5 cm. Color: 59A.

*Foliage description.*—Leaves simple, generally symmetrical, abundant, opposite or in whorls of three, horizontal to plant and flat in aspect. Size, largest leaves: Length: About 13 cm. Width: About 5 cm. Shape: Ovate with acuminate apex, attenuate base and ciliate margin. Texture: Smooth, glossy. Color: Young foliage, upper surface: 147A. Young foliage, lower surface: 59A. Fully expanded foliage, upper surface: Darker than 147A. Fully expanded foliage, lower surface: 59A. Venation, upper surface: 59A. Venation, lower surface: 59A. Petiole: Size: Length: About 3.5 cm. Diameter: About 3.5 mm. Color: 59A.

Flower description:

*Flower type and habit.*—Magenta-colored flowers. Freely and continuously flowering. Flowers arise from leaf axils. Usually ten to twelve flowers per lateral branch. Flowers positioned at or above the foliage and face upward or outward. Flowers slightly cupped to flat and rounded to rectangular. Flowers persistent.

*Flowering season.*—Year-round under greenhouse conditions. In the garden, flowering is continuous from spring until fall.

*Flower size.*—Length: About 7.3 cm. Width: About 6.5 cm. Depth: 5 to 6 mm.

*Flower buds.*—Size: Length: About 2.5 cm. Diameter: About 1.6 cm. Shape: Ovoid. Color: Slightly redder than 61B.

*Petals.*—Quantity: Five. Size (largest petals): Length: Top petal: About 3.4 cm. Middle petals: About 3.6 cm. Bottom petals: About 4.2 cm. Width: Top petal: About 5.7 cm. Middle petals: About 3.4 cm. Bottom petals: About 4.6 cm. Shape: Cordate with emarginate apex, cuneate or obtuse base and entire margin. Texture: Velvety, smooth. Color: When opening, upper surface: Iridescent, darker than 66A. When opening, lower surface: Iridescent, 57A. Fully opened, upper surface: Iridescent, slightly darker than 66A. Fully opened, lower surface: Iridescent, 57B. Fading to: 66A, upper petal becoming slightly blue.

*Spur.*—Length: 6 to 6.5 cm. Shape: Narrow and curved. Color: Proximal: 60A. Distal: 144B.

*Peduncles.*—Length: About 5 cm. Angle: Erect and outward. Strength: Strong. Color: 60B.

*Reproductive organs.*—Androecium: Stamen number: Five, anthers fused, filaments free. Anther shape: Obovate. Anther size: 6 by 4 mm. Anther color: Light cream. Amount of pollen: Moderate. Pollen color: Cream. Gynoecium: Five-loculate fused. Stigma color: White. Gynoecium length: About 6 mm. Gynoecium color: Darker than 59A.

Disease resistance: Under commercial conditions, resistance nor susceptibility to pathogens has not been observed.

Seed development: Seed production is not usually observed.

CHART A

| CHARACTERISTIC | 'JOLANA' | 'ANGUILLA' |
|---|---|---|
| GROWTH HABIT | Upright | Upright to slightly arching |
| VIGOR | Moderate to vigorous | Moderate |
| INTERNODE LENGTH | About 5.5 cm | About 4 cm |
| LEAF LENGTH | About 13 cm | About 10.5 cm |
| LEAF WIDTH | About 5 cm | About 4.5 cm |
| FLOWER POSITION | Flowers at or above the foliage | Flowers clearly above the foliage |
| QUANTITY OF FLOWERS PER LATERAL STEM | 10 to 12 | 8 to 10 |
| FLOWER LENGTH | About 7.3 cm | About 6.75 cm |
| FLOWER WIDTH | About 6.5 cm | About 6 cm |
| FLOWER DEPTH | 5 to 6 mm | About 4 mm |
| SPUR LENGTH | 6 to 6.5 cm | About 5.2 cm |
| PETAL COLOR, WHEN OPENING, UPPER SURFACE | Darker than 66A | Redder and darker than 57A |
| PETAL COLOR, WHEN OPENING, LOWER SURFACE | 57A | 57C |
| PETAL COLOR, OPENED, UPPER SURFACE | Slightly darker than 66A | Brighter and redder than 57A |
| PETAL COLOR, OPENED, LOWER SURFACE | 57B | 57B/57C |

It is claimed:

1. A new and distinct cultivar of New Guinea Impatiens plant, as illustrated and described.

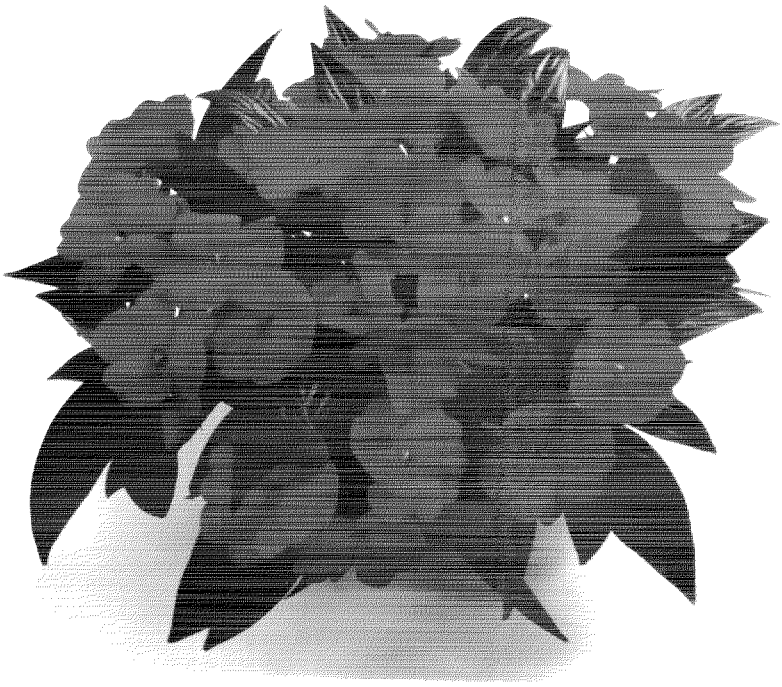

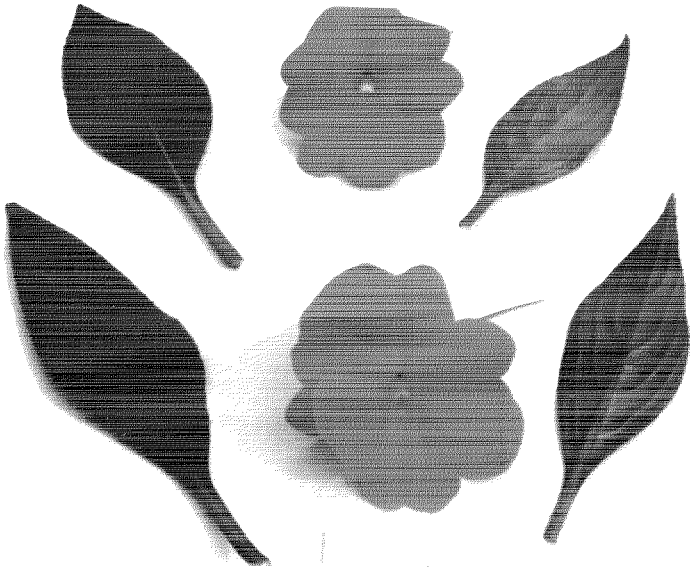

* * * * *